United States Patent
Dibello

(10) Patent No.: US 6,736,567 B1
(45) Date of Patent: May 18, 2004

(54) QUICK CONNECT APPARATUS AND METHOD FOR ORTHOTIC AND PROSTHETIC DEVICES

(75) Inventor: Thomas V. Dibello, Friendswood, TX (US)

(73) Assignee: Becker Orthopedic Appliance Company, Inc., Troy, MI (US)

( * ) Notice: Subject to any disclaimer, the term of this patent is extended or adjusted under 35 U.S.C. 154(b) by 205 days.

(21) Appl. No.: 09/665,800

(22) Filed: Sep. 20, 2000

Related U.S. Application Data

(62) Division of application No. 09/105,561, filed on Jun. 26, 1998, now Pat. No. 6,129,689.

(51) Int. Cl.[7] .................................................. A61F 5/00
(52) U.S. Cl. .......................... 403/353; 403/393; 606/99; 602/16; 128/80
(58) Field of Search .................................... 403/353, 393, 403/362; 128/80; 602/5, 16; 606/99

(56) References Cited

U.S. PATENT DOCUMENTS

| | | | |
|---|---|---|---|
| 4,379,463 A | 4/1983 | Meier et al. | |
| 4,732,143 A | 3/1988 | Kausek et al. | |
| 5,358,469 A | 10/1994 | Patchel et al. | |
| 5,561,736 A * | 10/1996 | Moore et al. | 704/260 |
| 5,672,152 A | 9/1997 | Mason et al. | |
| 5,743,910 A | 4/1998 | Bays et al. | |
| 5,851,194 A | 12/1998 | Fratrick | |
| 5,899,869 A | 5/1999 | Barrack, Jr. et al. | |
| 6,254,063 B1 * | 7/2001 | Rohde et al. | 256/13.1 |
| 6,298,629 B1 * | 10/2001 | Ador | 52/698 |
| 6,575,395 B2 * | 6/2003 | Rodriguez | 242/526.2 |

* cited by examiner

*Primary Examiner*—John R. Cottingham
(74) *Attorney, Agent, or Firm*—Ryndak & Suri

(57) ABSTRACT

A device is provided for releasably connecting together two elements of an orthosis or prosthesis. The device includes two plate members each attachable to a different orthotic element and a slider plate that is movable between a first released position and a second locked position. The device also may include a stop to secure the slider plate in the locked position.

15 Claims, 4 Drawing Sheets

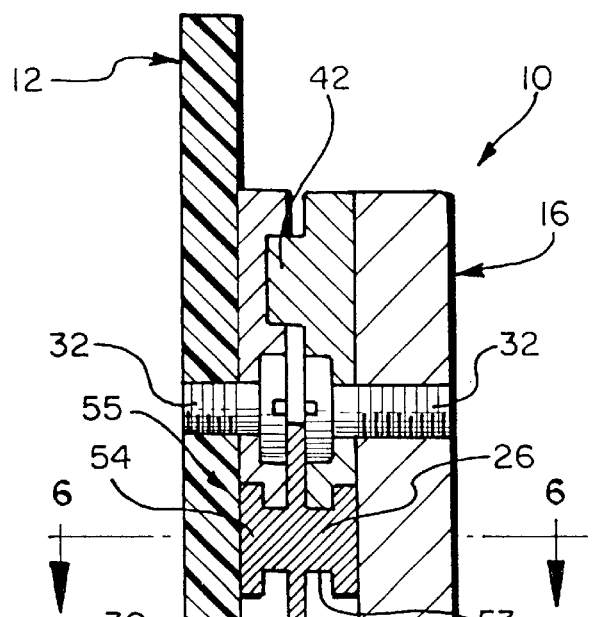
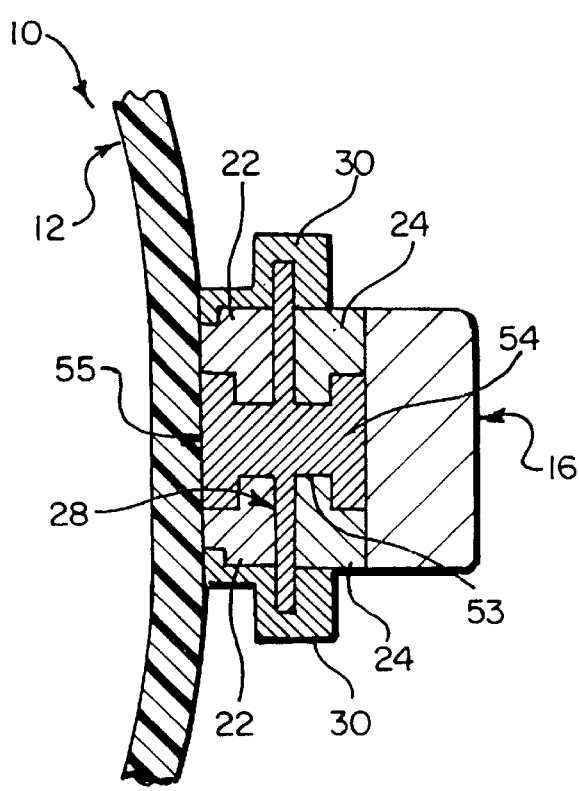

QUICK CONNECT APPARATUS AND METHOD FOR ORTHOTIC AND PROSTHETIC DEVICES

This application is a divisional of U.S. patent application Ser. No. 09/105,561, filed Jun. 26, 1998, now U.S. Pat. No. 6,129,689.

FIELD OF THE INVENTION

This invention relates to a device and method for releasably connecting together two elements of an orthotic or prosthetic device. More particularly, the invention relates to a quick connect apparatus that quickly and easily enables a user or an orthotist to attach an orthosis or prosthesis in an operative position.

BACKGROUND OF THE INVENTION

Orthotic and prosthetic devices traditionally have been utilized to aid in supporting, guiding and limiting the range of motion of different joints in the human body or to replace missing body joints and limbs or portions thereof. For example, if natural joints are congenitally defective or become defective due to disease or injury, an orthosis may be used. Typically, an orthotic device comprises two orthotic members or bars pivotally connected through a mechanical orthotic joint across, for example, the knee, elbow, wrist, hip, ankle, spine, torso or neck of a patient and mounted on opposite ends, such as for attachment to the foot, leg, arm, hand or neck of the body. These orthotic members are often custom fit specifically for an individual patient to some degree, such as by contouring a metal bar to a plaster mold of a patient's anatomy.

Orthotic devices are attached to the appropriate limb or body part by use of a leather or cloth strap, plastic band or cuff or similarly functioning device. Such device is firmly secured to the associated orthotic bar when the orthotic device is in use. In the past, orthotic members or bars have been directly and securely affixed to the straps by means of screws or other fasteners. It is often necessary or desirable for a patient to remove an orthotic device when the device is not needed, such as during sleep or bathing, for example. Additionally, a patient often needs to reconnect an orthotic device for use in certain activities. However, when the orthotic bar is rigidly attached to the strap, it is difficult and time consuming to remove or reconnect an orthotic device from and to the patient's limbs.

A need exists for a method of quickly and easily attaching orthotic members or bars to straps or other orthotic elements in a reliable manner. A need also exists for a readily releasable method of coupling the orthotic bars to the straps. A need further exists for such a readily releasable method of connecting orthotic bars to straps that is also sturdy and reliable for the user of an orthotic device and will not inadvertently disconnect when the orthotic device is in use. A need also exists for a method and device for quickly and easily attaching prosthesis members or elements together. As used herein, the term "appliance" shall mean an orthosis or orthotic device or a prosthesis or prosthetic device.

SUMMARY OF THE PRESENT INVENTION

One aspect of the present invention relates to releasably connecting two elements of an appliance (an orthotic or prosthetic device). In one embodiment, a sliding structure releasably connects to connecting members that in turn are attached to orthotic or prosthetic elements. The sliding structure is movable between two positions, namely released and locked positions. The user or orthotist can easily and quickly move the sliding structure to the locked or unlocked position and subsequently the orthotic or prosthetic device can be readily coupled or decoupled from the wearer. In accordance with another aspect of the present invention, a locking mechanism is provided that prevents the sliding mechanism from being moved from the locked position.

For purposes of the present invention, the terms "orthotic elements" and "appliance elements" refer to orthotic bars, orthotic straps, cuffs or bands, prosthetic limbs or any other members which are desired to be connected in an orthotic or prosthetic device.

In accordance with one aspect of the present invention, a device for releasably connecting together two elements of an orthosis or prosthesis is provided. The device includes a first member attachable to one orthotic element and a second member attachable to a second orthotic element. Sliding structure is provided that is capable of sliding movement for releasably connecting the first and second members in a predetermined relationship between a first released position that allows the first and second members to be separated and to a second locked position in which the first and second members are rigidly secured together in the predetermined relationship. The device also may include a stop mechanism for preventing movement of the sliding structure from the locked position. The stop structure may be composed of a plate member that is removably, fixedly mounted to at least one of the members that abuts the sliding mechanism. Alternatively, the stop mechanism may comprise a stop member insertable through the sliding mechanism and at least one of the first and second members to prevent relative movement of the sliding mechanism and that member, thereby maintaining the sliding mechanism in the locked position.

The sliding mechanism may be composed of a slider plate or body that includes an outwardly projecting flange for engaging and being guided by the first or second members. The slider plate may include a lug having an enlarged head spaced from the slider plate which prevents lateral movement of the slider plate relative to the first and second members when in the locked position.

More particularly, the second connecting member of the connecting device can include a slot extending parallel to the direction of sliding movement of the sliding mechanism, with the slot having a relatively wide portion and a relatively narrow portion, the wide portion providing the separating position and the narrow portion providing the locked position. The sliding mechanism may include a body portion having the lug projecting outwardly having one end attached to the body for traversing the slot and an enlarged head on the end of the lug opposite the end attached to the body for preventing lateral movement of the slider plate relative to the first and second members when in the locked position.

The sliding mechanism also may include at least one outwardly extending flange having a latch portion for retaining the body of the sliding mechanism on the first connecting member. The first connecting member also may have a complementary groove for retaining the flange of the body portion of the sliding mechanism.

The first member may have a first slot extending parallel to the direction of sliding movement of the sliding mechanism with the first slot having a relatively wide portion and a relatively narrow portion so that the narrow portion provides a locking position with respect to the first member.

In accordance with another aspect of the present invention, a device is provided for releasably connecting together two elements of an orthosis or prosthesis (an appliance). The device includes a pair of elongated plate members, each plate member being mountable to a different one of the two orthotic or prosthetic elements. Each of the elongated plate members has a pair of spaced-apart slots with each slot having a relatively wide portion defining a release position and a relatively narrow portion defining a locked position. A pair of sliding members are provided for linear sliding movement with respect to the slots of the elongated plate members. The sliding members include a body portion having opposed sides with a lug projecting from each side. Each lug has an enlarged head on the end of the lug located distally from the body portion. Each sliding member has at least one outwardly extending flange for guiding the sliding member during sliding movement along the elongated plate member. The sliding member is positionable with respect to the slots of the elongated plate members so that each of the lugs traverse one of the slots between the release and lock positions. The elongated plate members and sliding members cooperate so that for each of the sliding members, when one lug of each of the members is in a locked position, the other member is in the locked position. The device may further include a removable stop mechanism for preventing movement of the sliding members from the locked position. In one embodiment, the stop mechanism comprises a plate member removably, fixedly mounted to at least one of the elongated plate members with the stop mechanism abutting each of the sliding members.

In accordance with another aspect of the present invention, a method of releasably connecting together two elements of an orthosis or prosthesis is provided. First and second orthotic or prosthetic elements are provided having a first connecting member and second connecting member attached to a respective one of the orthotic or prosthetic elements. A sliding mechanism is provided that is capable of sliding movement for releasably connecting the first and second connecting members together in a predetermined relationship and movable between a first released position that allows the members to be separated and a second locked position in which the first and second members are rigidly connected together. The sliding mechanism is aligned in the released position and then is slided to the locked position to rigidly connect together the two elements.

In accordance with another aspect of the present invention, an orthosis is provided that includes the previously described device for releasably connecting together two elements of an orthosis. The orthosis includes an orthotic joint and first and second orthotic elements connected to first and opposed parts of the orthotic joint.

In accordance with another aspect of the present invention, a slider member is provided that is especially adapted for use in a device for releasably connecting together two elements of an appliance (an orthosis or prosthesis). The slider plate member includes a body portion having lugs extending outwardly from opposed sides of the body portion. Each of the lugs has an enlarged head portion at the distal lug end and has flanges extending from upper and lower areas of the body on opposed sides of the body.

BRIEF DESCRIPTION OF THE DRAWINGS

FIG. 5 is a sectional view of the quick connect device of the present invention in locked position taken along line 5—5 of FIG. 1; and FIG. 6 is a sectional view of the quick connect device of the present invention taken along line 6—6 of FIG. 5.

DETAILED DESCRIPTION

Figure 1:
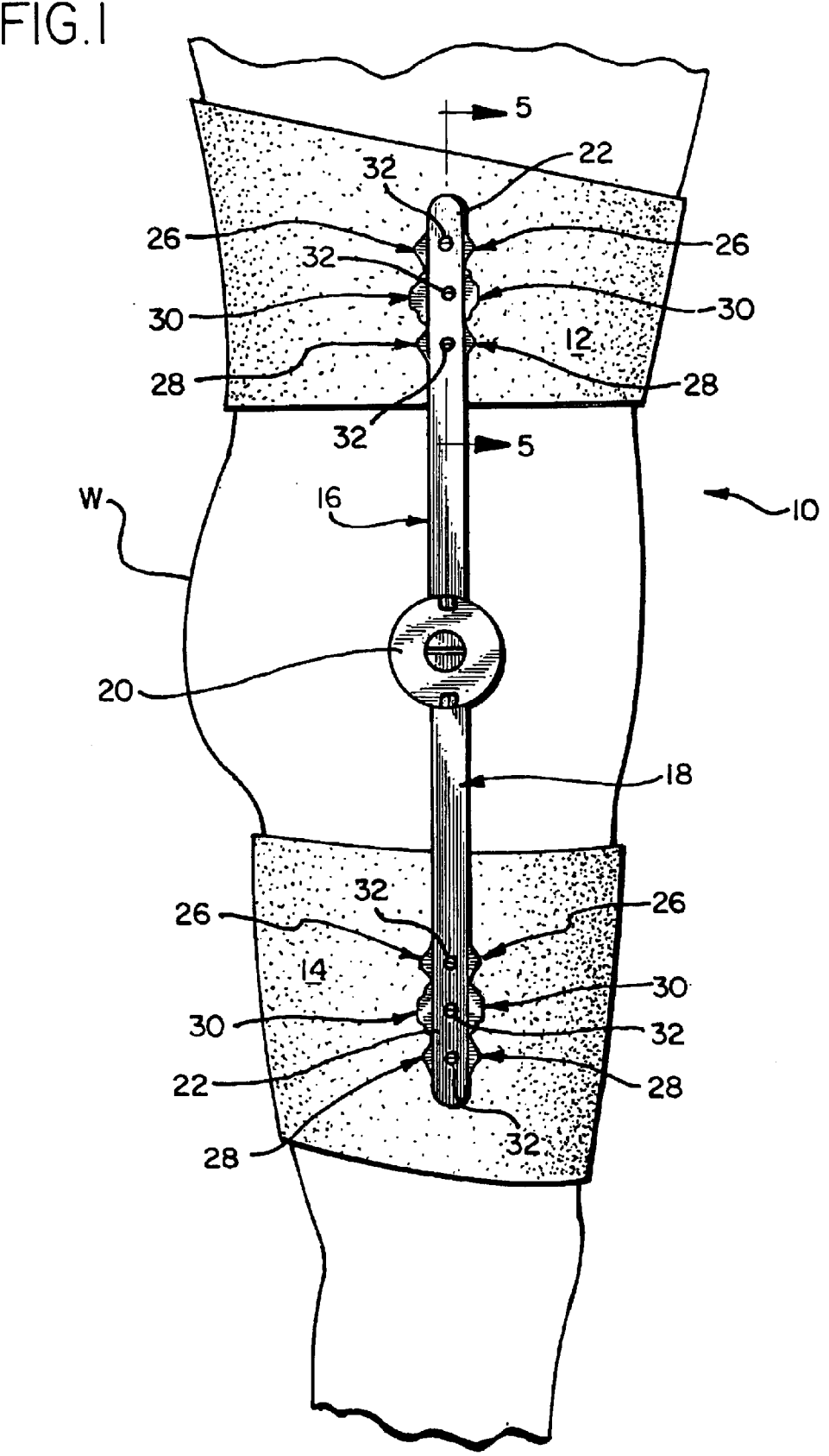
FIG. 1 is a side elevation view of an appliance device in accordance with the present invention.

Referring to the figures generally, and particularly to FIGS. 1, 2, 5 and 6, there is illustrated an appliance device 10 in accordance with the present invention on a person W wearing device 10. Appliance device 10 is a hip orthosis that is easily connected and secured in a locked position and removed when desired. In addition, when desired, appliance device 10 can be reassembled and reattached quickly by a person W wearing device 10.

Although the described embodiment of the present invention is in the context of a hip orthosis, the present invention is also applicable to many different orthoses, including ankle, elbow and neck orthotic devices, for example. Hip orthosis 10 in accordance with the present invention is composed of a pelvic section 12 and a thigh cuff 14, orthotic bars 16 and 18, mechanical joint 20, elongated plate members 22 and 24, slider plates 26 and 28, stop 30, and fasteners 32.

For a hip orthotic device, pelvic section 12 and thigh cuff 14 may extend completely around a patient's torso and thigh respectively. Pelvic section 12 and thigh cuff 14 are attached to a user by suitable straps. Pelvic section 12 and thigh cuff 14 may be constructed of leather, cloth, plastic, combinations thereof or any suitable material as is well known in the art to properly secure the orthotic device to the patient. Orthotic bars 16 and 18 are typical orthotic bars as is known to those skilled in the art and may be situated substantially longitudinally with respect to a patient's limb and torso. Orthotic bar 16 terminates at one end at joint 20 and at the other end at pelvic section 12. Similarly, orthotic bar 18 terminates at thigh cuff 14 at one end and at joint 20 at the other end. Mechanical joint 20 pivotally connects orthotic bar 16 and orthotic bar 18 and allows relative pivotal movement through a predetermined range of motion.

Orthotic bar 16 is solidly and rigidly secured to plate member 22 by use of fasteners 32. Any number and type of fasteners may be used, such as for example, nuts, bolts, adhesives, etc. Similarly, plate member 24 is rigidly mounted to thigh cuff 14 by fasteners or any suitable mounting structure. Plate member 22 is releasably secured to plate member 24 by slider plates 26 and 28 and is maintained in a locked position by use of stops 30.

Figure 2:
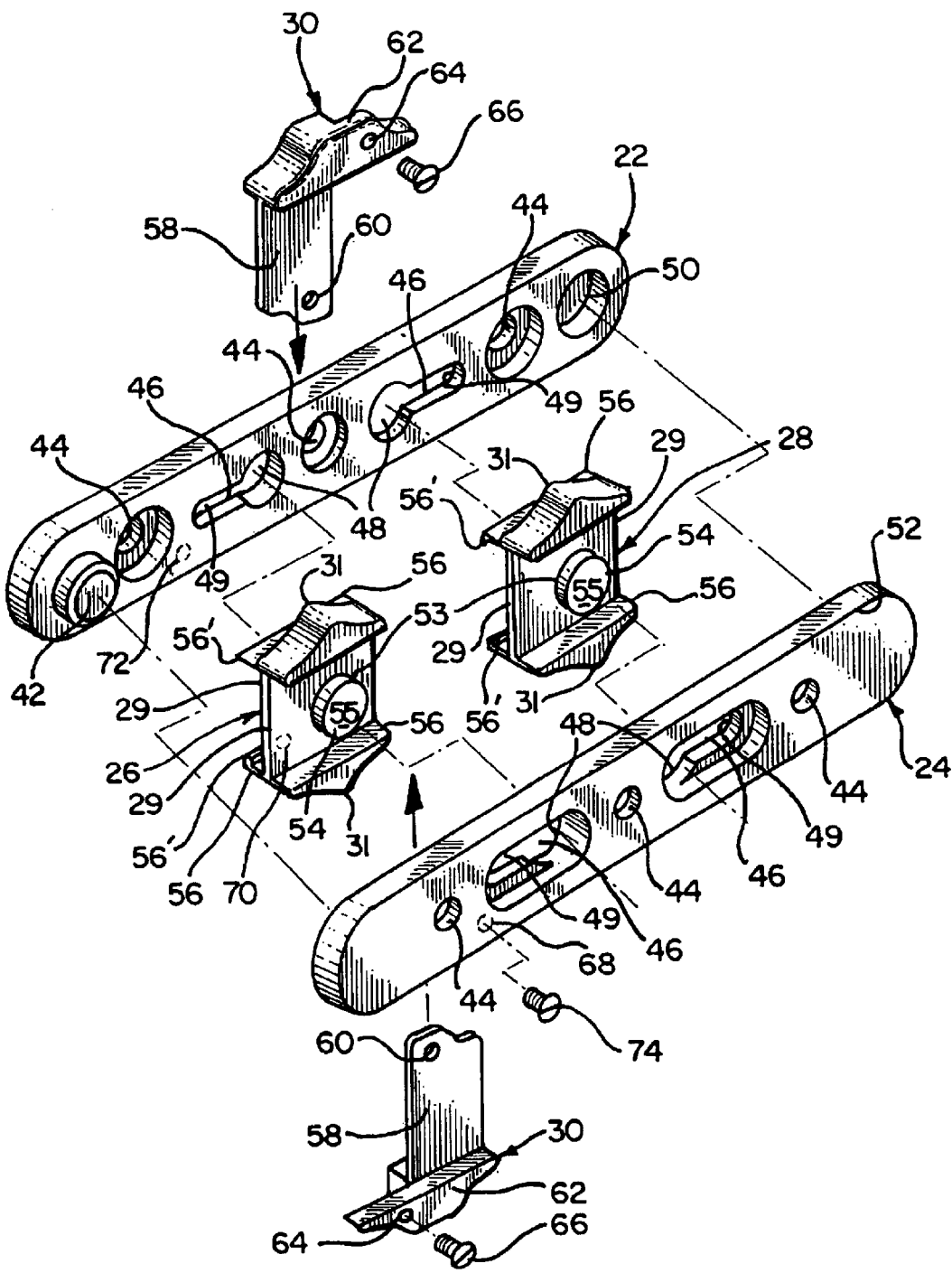
FIG. 2 is a perspective exploded view of a portion of the appliance device of the present invention illustrating the quick connect device of the present invention.

Turning now to FIG. 2, there is illustrated elongated plate members 22 and 24, slider plates 26 and 28 and stops 30. An identical set of plate members and slider plates connect each strap to its corresponding bar, i.e., pelvic section 12 and orthotic bar 16. Alternatively, larger, smaller, or different shaped components may be used depending upon the materials of the orthotic elements and the location of the connection, among other things. Alternatively, pelvic section 12 partly shown in FIGS. 5 and 6 may be a portion of a prosthesis. Plate members 22 and 24 are made of metal, plastic or any other suitably strong material to be capable of securely mounting to the orthotic elements. Plate members 22 and 24 may be of any shape, preferably elliptical or rectangular.

Plate members 22 and 24 include a finger 42, holes 44, slots 46 and recessed opening 50 which is complementary to finger 42. Plate members 22 and 24 may but need not be identical. Plate members 22 and 24 preferably have certain elements that are complementary to fit together more securely. For example, finger 42 of plate member 22 fits into recessed opening 50 of plate member 24 to help secure the plate members 24 and 22 together and prevent lateral movement thereof. Holes 44 receive fasteners 32 to rigidly secure each plate member to its corresponding orthotic element. Slots 46 extend parallel to the direction of sliding movement of slider plate 26, as described in detail herein. Any desired number of spaced apart slots may be used with the present invention, and in the described embodiment there are a pair of slots 46 on plate member 22. Slots 46 have a relatively wide portion 48 and a relatively narrow portion 49. Lugs 55 mounted on opposed sides of plates 26 and 28 traverse slots 46. Relatively wide portion 48 is circular and slightly larger than enlarged head 54 of lug 55. Finally, plate members 22 and 24, in the described embodiment, contain a groove 52 on the top extending substantially the entire length of each plate member 22 and 24 to guide sliding plates 26 and 28 in linear movement. Groove 52 optionally may be present along the bottom edge of plates 22 and 24.

Slider plates 26 and 28 have a planar body portion 29 with lug 55 projecting outwardly from opposite sides of the body. Lug 55 can be of any cross-sectional shape such as for example, circular, oval or square. Lug 55 has a relatively narrow end 53 for traversing slot 46 and an enlarged head 54 on the end of lug 55 located distally from the body. Enlarged head 54 is slightly smaller than slot 46 and narrow end 53 is slightly smaller than relatively narrow portion 49 of slot 46. Additionally, the length of lug 55 is at least slightly longer than the depth of plate member 22.

Figure 4:
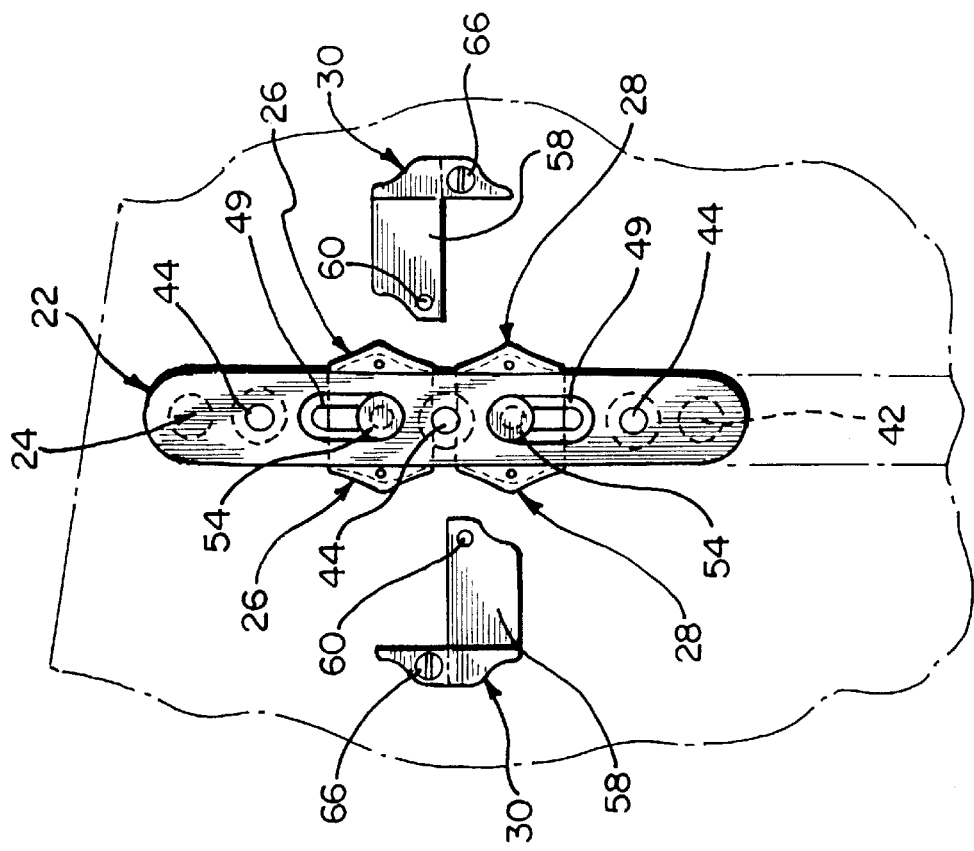
FIG. 4 is a side elevation view of a portion of the appliance device of the present invention showing the quick connect device in the unlocked position.
Figure 3:
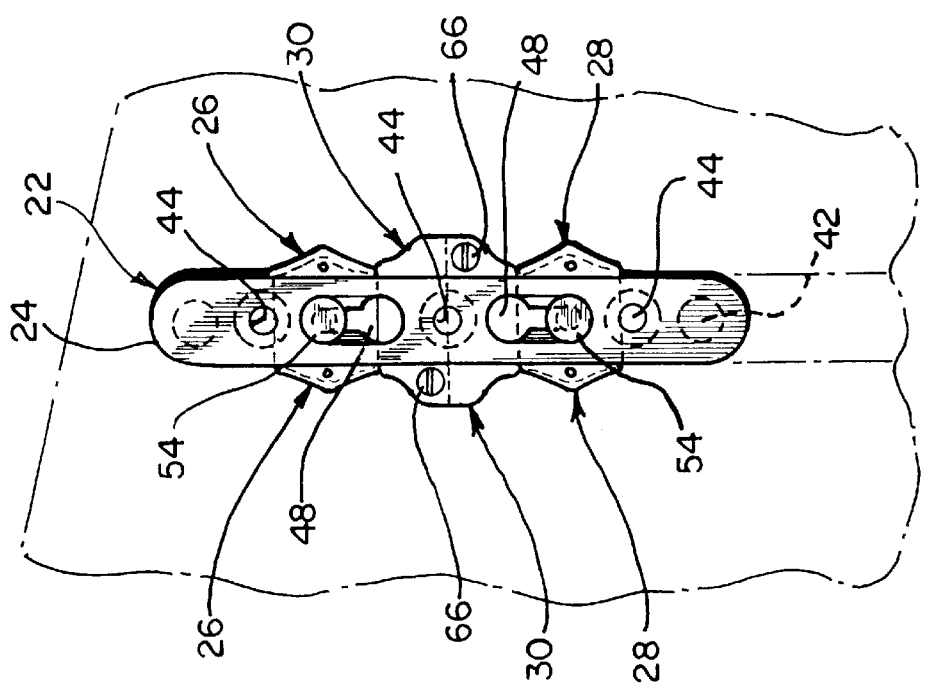
FIG. 3 is a side elevation view of a portion of an appliance device of the present invention showing the quick connect device in the locked position.

To connect plate member 22 to plate member 24, the extending portions of lug 55 are inserted into slots 46 on both plate members 22 and 24. Lug 55 extends through relatively wide portion 48 and at least a portion of lug 55 extends beyond the depth of plate members 22 and 24. Upon insertion, plate members 22 and 24 are oriented together but are easily detachable. This is the released or unlocked position of the present invention and is illustrated in FIG. 4.

Slider plates 26 and 28 also have a triangular top and bottom portion with flanges 56 extending normal to body portion 29. Flange 56 has a lip 56' that is complementary to and may engage and ride on grooves 52 to allow slider plates 26 and 28 to move freely laterally across plate members 22 and 24 respectively. Flange 56 and lip 56' may snap in place on groove 52. Grooves 52 also guide and retain slider plates 26 and 28 along plate members 22 and 24 during sliding. The triangular top or bottom portion 31 of slider plates 26 and 28 can be moved and grasped easily by any suitable means such as by a human finger. Top and bottom portions 31 may be any shape that permits easy grasping or use by the finger of a user. Top and bottom portions 31 of slider plate 26 prevent lateral movement of the slider plate relative to plate members 22 and 24. After lug 55 is inserted into relatively wide portion 48, slider plates 26 and 28 can freely move across slots 46. Narrow portion 53 of lug 55 can move within relatively narrow portion 49 of slot 46. When lug 55 is moved to narrow portion 49 of slot 46, the present invention is in the locked position as illustrated in FIG. 5 and the lug 55 prevents lateral movement of slider plate 26 relative to plate members 22 and 24. Until secured by stops 30, slider plates 26 and 28 are freely moveable between the locked and released positions. Slider plates 26 and 28 and plate members 22 and 24 cooperate in such a manner that when lug 55 of slider plate 26 is in the locked position, lug 55 of slider plate 28 is also in the locked position.

Alternatively, slider plates 26 and 28 may be rigidly fixed to plate members 22 and 24 respectively. In such embodiment, plate members 22 and 24 can easily be releasably connected directly to each other.

Stops 30 are used to secure slider plates 26 and 28 in locked position relative to plate members 22 and 24. Stops 30 may include a snap fit relationship between narrow end 53 of lug 55 and relatively narrow portion 49, insertable fasteners, a plate member(s) or any suitable structure to prevent movement of slider plates 26 and 28 relative to plate members 22 and 24.

As illustrated in FIGS. 4 and 5, stops 30 are a pair having a substantially planar portion 58 with hole 60 for insertion between slider plates 26 and 28. Planar portion 58 also may have a handle 62, to readily permit handling, extending therefrom with hole 64 therein. After slider plates 26 and 28 have been moved to the locked position, planar portion 58 of stops 30 are inserted between the slider plates. Hole 60 of planar portion 58 of one of stops 30 is aligned with hole 64 of handle 62 of the other plate member. Stops 30 abut and press against slider plates 26 and/or 28 to prevent lateral movement.

Finally, fastener 66 may be used to removably fixedly secure the stops 30 in position, thereby removably securing the entire orthotic or prosthetic device. To release the orthotic or prosthetic device, one only needs to unfasten fastener 66 and remove the stops. At this point, slider plates 26 and 28 can be moved to the unlocked position. The orthotic or prosthetic elements can then easily be separated.

Alternatively, a stop member may be inserted directly into slider plates 26 and/or 28 and at least one of plate members 22 and 24 to prevent relative movement of the slider plate and that member plate. The stop member maintains the device in the locked position. Such stop members may include any suitable fastener or latch. For example, as illustrated in dotted lines in FIG. 2, aligned holes 68, 70 and 72 may be provided in elongated plate members 24, slider plate 26 and elongated plate member 22, respectively. A threaded fastener 74 may then be utilized to secure slider plate 26 when in a locked position relative to plate members 22 and 24.

It should be understood that any number of lugs, slots and slider plates can be used in accordance with the present invention. For example, there may be four sets of each. Alternatively, only one slider plate may be used with one or two slots per plate member.

While the invention has been described with respect to certain preferred embodiments and, as will be appreciated by those skilled in the art, it is understood that the invention is capable of numerous changes, modifications and rearrangements, and such changes, modifications and rearrangements are intended to be covered by the following claims.

What is claimed is:

1. A device for releasably connecting together two elements of an appliance, comprising:
   a first elongated member attachable to one appliance element, the first elongated member having a slot;
   a second elongated member attachable to a second appliance element, the second elongated member having a slot, each slot having a relatively wide portion and a relatively narrow portion; and
   a sliding member for releasably connecting the first elongated member to the second elongated member, the sliding member having opposing sides with a projecting member extending from each side, one of the projecting members insertable into a wide portion of one of the slots and the other of the projecting members insertable into the other one of the slots, the sliding member positionable between the elongated members and the projecting members being movable between the respective wide and narrow portions of the slots, to rigidly secure the elongated members together when the projecting members are located in the narrow portions of the respective slots.

2. The device of claim 1 further comprising a removable stop member for preventing movement of said sliding member from said narrow portion.

3. The device of claim 2 wherein said stop member comprises a plate member removably fixedly mounted to at least one of said elongated members that abuts said sliding member.

4. The device of claim 2 wherein said stop member is insertable through said sliding member and at least one of said elongated members to prevent relative movement between the sliding member and one of said elongated members.

5. The device of claim 1 wherein said sliding member further comprises a flange that engages said first elongated member.

6. The device of claim 1 wherein the wide portions allow the elongated members to be separated and the narrow portions provide a locked position.

7. The device of claim 6 wherein each protecting member has an enlarged head on an end opposite the sliding member for traversing each slot.

8. The device of claim 7 wherein said enlarged heads prevent lateral movement of said sliding member relative to said first and second elongated members when in said locked position.

9. The device of claim wherein said sliding member further comprises a body portion and at least one outwardly extending flange for retaining said body portion on said first elongated member.

10. A device for releasably connecting together two elements of an appliance comprising:
  a pair of elongated plate members, each mountable to a different one of said two appliance elements, each of said elongated plate members having a pair of spaced apart slots, each slot having a relatively wide portion defining a release position and a relatively narrow portion defining a lock position;
  a pair of sliding members for linear sliding movement with respect to the slots of said elongated plate members comprising:
    a body portion having opposed sides with a lug projecting from each side, each lug having an enlarged head on the end of the lug located distally from said body portion, each sliding member having at least one outwardly extending flange for guiding said sliding member during sliding movement along said elongated plate members, said sliding member being positionable with respect to the slots of said elongated plate members so that each of said lugs traverse one of said slots between said release and lock positions, said elongated plate members and sliding members cooperating so that for each of said sliding members when one lug of each of said members is in a locked position the other lug of said member is in a locked position.

11. The device of claim 10 further comprising removable stop for preventing movement of said sliding members from the locked position.

12. The device of claim 11 wherein said stop comprises a plate member removably fixedly mounted to at least one of said elongated plate members, said stop abutting each of said sliding members.

13. A slider member for releasably connecting two appliance elements comprising:
  a body portion having opposing sides, and a projecting member extending outwardly from each side of the body portion, each of said projecting members having an enlarged head portion at the distal end;
  flanges on opposed sides of the body, said flanges extending outwardly substantially perpendicular to said body portion; and a protuberance extending from at least one of said flanges.

14. The device of claim 1 wherein the first elongated member further comprises a finger and the second elongated member further comprises a recess adapted to receive the finger, the finger and the recess brought into cooperation when the projecting members are moved into the narrow portions.

15. A device for releasably connecting two elements of an appliance comprising:
  a first elongated member attachable to a first appliance element, the first elongated member having a slot and a finger;
  a second elongated member attachable to a second appliance element, the second elongated member having a slot, a recess corresponding to the finger, each of said slots having a relatively wide portion and a relatively narrow portion; and
  a sliding member having opposed sides and a projecting member on each of said opposed sides, the sliding member moveable along the slots of the first and second elongated members and one of the projecting members of the sliding member insertable into the wide portion of one of the slots and the other of the projecting members of the sliding member insertable into the wide portion of the other slot, each projecting member moveable between the wide and narrow portions of the associated slot, wherein moving the projecting members into the narrow portion of the associated slot brings the finger into cooperation with the recess and rigidly secures the elongated members together.

* * * * *

UNITED STATES PATENT AND TRADEMARK OFFICE
CERTIFICATE OF CORRECTION

PATENT NO. : 6,736,567 B1  
APPLICATION NO. : 09/665800  
DATED : May 18, 2004  
INVENTOR(S) : Dibello Page 1 of 1

It is certified that error appears in the above-identified patent and that said Letters Patent is hereby corrected as shown below:

On Title page (item 56) under "References Cited" the following patents should be listed under U.S. Patent Documents:

3,986,318 *      10/1976      McConnell      403/353x  
    4,225,265 *      09/1980      Hooker et al.      403/353  
    5,161,268 *      11/1992      Harrow      403/393x  
    6,494,853 *      12/2002      Rossi et al.      602/19x Column 4, line 5, after "in" insert --the--.  
Column 6, line 37, delete "members" and insert therefor --member--.  
Column 7, claim 7, line 1, delete "protecting" and insert therefor --projecting--.  
Column 7, claim 9, line 1, after "claim" insert --7--.  
Column 8, claim 11, line 1, after "comprising" insert --a--.

Signed and Sealed this

Twenty-ninth Day of August, 2006

JON W. DUDAS  
*Director of the United States Patent and Trademark Office*